United States Patent [19]

Gerster et al.

[11] Patent Number: 4,603,199
[45] Date of Patent: Jul. 29, 1986

[54] PHENYL-SUBSTITUTED TRICYCLIC ANTIBACTERIAL AGENT INTERMEDIATES

[75] Inventors: John F. Gerster; Richard M. Stern, both of St. Paul, Minn.

[73] Assignee: Riker Laboratories, Inc., St. Paul, Minn.

[21] Appl. No.: 574,045

[22] Filed: Jan. 26, 1984

Related U.S. Application Data

[62] Division of Ser. No. 436,376, Oct. 25, 1982, Pat. No. 4,443,447.

[51] Int. Cl.$^4$ .................. C07D 215/04; C07D 215/12; C07D 241/42; C07D 265/36
[52] U.S. Cl. .................................. 544/105; 544/353; 546/165; 546/166
[58] Field of Search ................ 544/105, 353; 546/165, 546/166

[56] References Cited

U.S. PATENT DOCUMENTS 4,348,521  9/1982  Gerster ................................. 544/353

Primary Examiner—Richard L. Raymond
Attorney, Agent, or Firm—Donald M. Sell; James A. Smith; Robert W. Sprague

[57] ABSTRACT

Antimicrobial compounds of the following formula are disclosed:

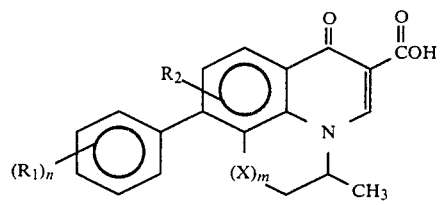

wherein X is selected from the group consisting of —O—, —CH$_2$ and

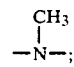

m is 0 or 1; R$_1$ is selected from the group consisting of hydrogen, nitro, amino, lower alkyl, lower alkanamido, lower N,N-dialkylamino, formamido, hydroxy, lower alkoxy, halogen, lower haloalkanamido and pyrryl; n is 1 or 2; and R$_2$ is selected from the group consisting of hydrogen, methyl, fluoro, chloro and nitro. Acyl chlorides, esters, alkylaminoalkyl ester salts, amides and pharmaceutically acceptable carboxylate salts are also disclosed. Pharmaceutical compositions containing these compounds, methods of using these compound and synthetic intermediates are also disclosed.

2 Claims, No Drawings

PHENYL-SUBSTITUTED TRICYCLIC ANTIBACTERIAL AGENT INTERMEDIATES

This is a division of application Ser. No. 436,376 filed Oct. 25, 1982, now U.S. Pat. No. 4,443,447.

TECHNICAL FIELD

This invention relates to derivatives of tricyclic heterocyclic ring systems. More specifically, it relates to compounds with quinolizine, benzoxazine, quinoxaline and pyrroloquinoline ring systems substituted by an optionally substituted phenyl ring. The use of these compounds as antimicrobial agents, pharmaceutical compositions containing the compounds and synthetic intermediates useful in preparing the compounds are also included within the scope of the invention.

BACKGROUND OF THE INVENTION

U.S. Pat. No. 3,472,859 describes 1-alkyl-1,4-dihydro-4-oxo-3-quinolinecarboxylic acids which are substituted in the 6 or 7 position with a phenyl group.

U.S. Pat. Nos. 3,896,131 and 3,985,882 describe benzo[ij]quinolizine-2-carboxylic acids which are useful antimicrobial agents. These compounds may contain various non-phenyl substituents at the 8, 9 or 10 positions of the benzo ring.

U.S. Pat. No. 3,883,522 describes pyrido[1,2,3-de]-1,4-benzoxazine-6-carboxylic acids which are useful antimicrobial agents. These compounds may contain various non-phenyl substituents on the benzo ring.

The compound 2,3-dihydro-3-methyl-7-oxo-1H,7H-pyrido[1,2,3-de]quinoxaline-6-carboxylic acid is reported by Stevens, J. of Antimicrobial Chemotherapy (1980), 6, 535–542, to be a bacteriostatic compound.

Pyridoquinoxalines are described in assignee's copending application U.S. Ser. No. 254,973, now U.S. Pat. No. 4,348,521, assigned to the same assignee as the present invention. Pyridoquinoxalines having phenyl substituents at the 10 position of the benzo ring are not disclosed.

U.S. Pat. No. 3,917,609 describes pyrrolo[3,2,1-ij]quinoline-5-carboxylic acids which are useful as antibacterial agents. These compounds may contain various non-phenyl substituents on the benzo ring.

Japanese laid-open patent publication No. 55-118416 describes 8-(1-piperazinyl)-6,7-dihydro-1-oxo-1H,5H-benzo[ij]quinolizine-2-carboxylic acids.

DESCRIPTION OF THE INVENTION

This invention relates to tricyclic compounds which are useful as antimicrobial agents. The invention also relates to a method for combatting microbial infections comprising contacting the microorganisms with an effective amount of a tricyclic compound of the invention and to pharmaceutical compositions comprising both an effective amount of a tricyclic compound of the invention and a pharmaceutically acceptable carrier. This invention also relates to synthetic intermediates useful in preparing the tricyclic compounds of the invention.

Specifically, the invention relates to compounds of the formula

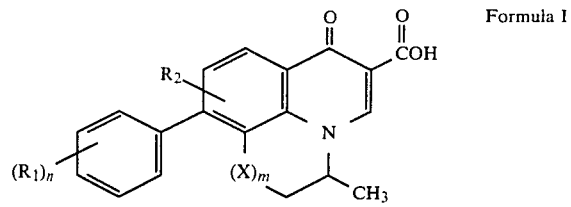

Formula I wherein X is selected from the group consisting of —O—, —CH$_2$—, and

m is 0 or 1; R$_1$ is selected from the group consisting of hydrogen, lower alkyl, nitro, amino, lower alkanamido, lower N,N-dialkylamino, formamido, hydroxy, lower alkoxy, halogen, lower haloalkanamido, and pyrryl; n is 1 or 2; and R$_2$ is selected from the group consisting of hydrogen, methyl, fluoro, chloro and nitro. The acyl chloride, esters, alkylaminoalkyl ester salts, amides and pharmaceutically acceptable carboxylate salts of the compound of Formula I are also included within the scope of the invention.

The term "lower" as used herein to describe "alkyl" designates an alkyl group containing 1 to about 4 carbon atoms in straight or branched chain configuration. All alkyl groups of the compounds of the present invention are lower alkyl. Preferred lower alkyl groups are methyl and ethyl groups.

Compounds of the invention have an optically active carbon. This optically active carbon is at the position numbered 5 in the quinolizine ring system, 3 in both the benzoxazine and quinoxaline ring systems, and 2 in the pyrroloquinoline ring system. All such optical isomers are included within the scope of the invention.

Compounds of the invention may be named in several ways. Using the most commonly acceptable system of the International Union of Pure and Applied Chemistry the systems are numbered as shown below:

2,3-dihydro-3-methyl-7-oxo-10-phenyl-7H—pyrido[1,2,3-de]-1,4-benzoxazine-6-carboxylic acid system:

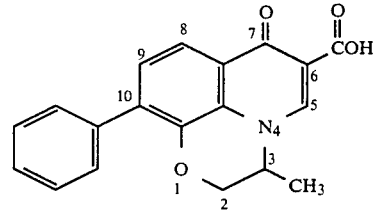

6,7-dihydro-5-methyl-1-oxo-8-phenyl-1H,5H—benzo[ij]quinolizine-2-carboxylic acid system:

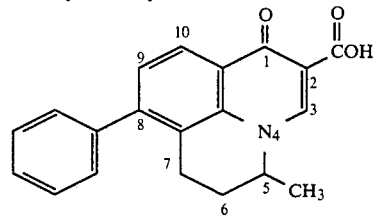

2,3-dihydro-3-methyl-7-oxo-
10-phenyl-1H,7H—pyrido-
[1,2,3-de]quinoxaline-6-
carboxylic acid system:

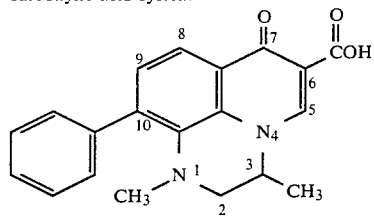

1,2-dihydro-2-methyl-6-
oxo-9-phenyl-6H—pyrrolo-
[3,2,1-ij]quinoline-5-
carboxylic acid system:

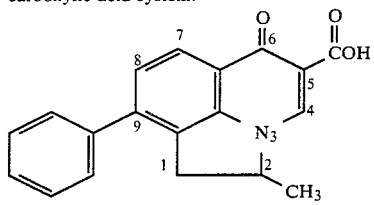

Preferred compounds of the present invention are the pyrido[1,2,3-de]-1,4-benzoxazines and the benzo[ij]-quinolizines. Preferred compounds of the invention are those wherein $R_1$ is hydrogen, halogen, hydroxy, nitro, amino, methoxy, ethoxy, formamido, acetamido, N,N-dimethylamino, haloalkanamido and pyrryl; n is 1 or 2; and $R_2$ is hydrogen, methyl or halogen.

It is well known in the art that pharmaceutically acceptable salts such as alkali metal, alkaline earth, aluminum, iron, silver and other metal and amine salts of pharmaceutically active acids are the equivalents of the corresponding acids, and in some cases may even offer advantages in absorption, formulation or the like. Salts of the free acid compounds of the invention are readily prepared by reaction of the acid with a base and evaporation to dryness. The base may be organic, e.g., sodium methoxide or an amine, or inorganic, e.g., sodium hydroxide.

Esters of the acids of Formula I may be obtained as intermediates during the preparation of the acids, or, in some cases, the esters may be prepared directly from the acid using standard synthetic methods. The esters exhibit antimicrobial activity but are primarily of interest as synthetic intermediates. In some instances, hydrolyzable or salt-forming esters may be of interest as therapeutic agents. Preferred esters of the invention are alkyl esters and alkylaminoalkyl esters. Especially preferred are alkylaminoalkyl esters such as dimethylaminoethyl esters which form salts, e.g., hydrochlorides.

In preparing the esters of the invention from the free acid of Formula I, the free acid of Formula I is reacted with thionyl chloride to provide the novel acyl chloride derivative. The acyl chloride is subsequently reacted with the appropriate alcohol to provide the desired ester.

The amides of the invention are prepared readily by reacting the acyl chlorides of the invention with ammonia to provide primary amides, with primary alkylamines to provide secondary amides, or with secondary alkylamines to provide tertiary amides.

The antimicrobial activity of the compounds of the present invention can be demonstrated by the known, standard plate dilution method for bacterial susceptibility to antibiotics. The culture medium employed permits susceptibility testing of fastidious microorganisms towards antibiotics, sulfonamides and other chemotherapeutic agents. Tryptone soy agar (oxoid) of the following composition is the culture medium.

| | |
|---|---|
| Oxoid tryptone | 15 g |
| Oxoid soy peptone | 5 g |
| Sodium chloride | 5 g |
| Oxoid agar-agar No. 3 | 15 g |
| Water | 1 liter |

Using this test, the compounds of the invention have been found to have a broad spectrum of activity against gram-positive and gram-negative microorganisms.

The compounds of the invention are active against microorganisms either in the absence or presence of 10 percent horse serum.

The test procedure used to determine activity as employed in connection with the present invention provides information on the amount of a compound required to give complete inhibition, partial inhibition or no inhibition of microbial growth on the agar plates. In the tests, the test compound is added to the agar medium to give concentrations of zero, one, ten and one hundred milligrams per liter. A series of plates with these concentrations is prepared. Ten percent horse serum is added to one series of such plates. Aliquots of broth culture of each of twelve species of microorganisms are innoculated onto the agar plates containing the various test compound concentrations. The plates are incubated at 37° C. in a 10 percent carbon dioxide atmosphere for 18-24 hours. The microbial growth on each plate is read visually, and minimal partial or complete inhibitory concentrations are recorded. Some of the microorganisms which are used for this test are:

1. *Staphylococcus aureus*
2. *Bacillus subtilis*
3. *Escherichia coli*
4. *Pseudomonas aeruginosa*
5. Streptococcus sp.*
6. *Aspergillus niger*
7. *Candida albicans*
8. *Acinetobacter lwoffi*
9. *Acinetobacter anitratum*
10. *Klebsiella pneumoniae*
11. *Streptococcus fecaelis*
12. *Serratia marcescens*

*strains isolated from dental caries rats or hamsters at the National Institute of Dental Health and grown in PFY or APT agar.

The compounds of the invention possess antimicrobial activity towards one or more of the above microorganisms.

Some of the compounds of the invention have also been tested and have been found to exhibit activity against one or more anaerobic bacteria, for example, Bacteroides sp. and *Clostridium welchii*. Some compounds of the invention have shown useful activity towards *Erwinia amylovora*, a gram-negative microorganism responsible for the plant disease known as fire blight.

It will be understood by those skilled in the art that the species used are representative indicator species, as it would be impractical to screen against all microorganisms. It is well known in the art that broad spectrum activity can be predicted on the basis of activity shown against selected representative species of microorganisms.

Some of the compounds of the invention have been tested and have been found to be active when administered orally to animals. They are excreted in the urine, and are effective urinary tract antibacterials in mammals. It is also contemplated that they may be used in the treatment of pulmonary infections, soft tissue infections, burn infections and bacteremias.

The compounds of the invention are active against microorganisms in vitro or topically. In vitro activity is useful in itself, since antimicrobial agents may be used for disinfecting and sterilizing medical and dental equipment and the like.

The compounds of the invention are also active in vivo in animals. The acute oral toxicity of the compounds of the invention is generally moderate to low compared with the effective oral dose, and they have an acceptable therapeutic ratio ($LD_{50}/ED_{50}$).

The carboxylic acid compounds of the invention are ordinarily white or yellowish crystalline or amorphous materials when purified. They are substantially insoluble in water, lower alcohols and hydrocarbons and are generally more soluble in halogenated solvents, N,N-dimethylformamide and the like. The esters are generally somewhat more soluble in organic solvents. The salts, especially the alkali metal salts, have appreciable solubility in water and lower alcohols.

The compounds of the invention may be formulated by incorporating them into conventional pharmaceutical vehicles, either organic or inorganic, which are suitable for oral or intraperitoneal application. For in vitro or topical use, simple aqueous solutions or suspensions are particularly convenient. For these purposes, concentrations of a compound of the invention on the order of 100 parts by weight per one million parts by weight of water up to about 5 parts by weight per one thousand parts by weight of water are suitable, and the formulation is used by immersing objects to be treated therein, or by local application to an infected area.

The amount of compound to be used to treat, for example, a microbial urinary infection by oral administration will be an effective amount and less than a toxic amount. As is well-known to those skilled in the medical arts, the amount to be administered to control an infection will depend on the species, sex, weight, physical condition and many other factors. Usually the amount will be less than 100 mg/kg per dose. Conveniently, this is administered in the form of conventional pharmaceutical preparations such as capsules, tablets, emulsions, solutions and the like. Excipients, fillers, coatings, etc. are generally employed with tablets or capsules, as is well known in the art.

It is known to the art that antimicrobial agents are useful as growth promoters in various animal and bird species. Although not yet verified, it is inferred from the outstanding antimicrobial activity that the compounds of the invention can be used for this purpose also. The compounds of the invention may also be used for the control of microbial (e.g., Erwinia amylovora) infections of plants, e.g., by spraying or dusting formulations of these compounds on the affected area.

The compounds of the invention are prepared starting with known compounds.

The benzoxazines of the invention of Formula I are prepared as illustrated generally in Reaction Scheme 1 below:

REACTION SCHEME I

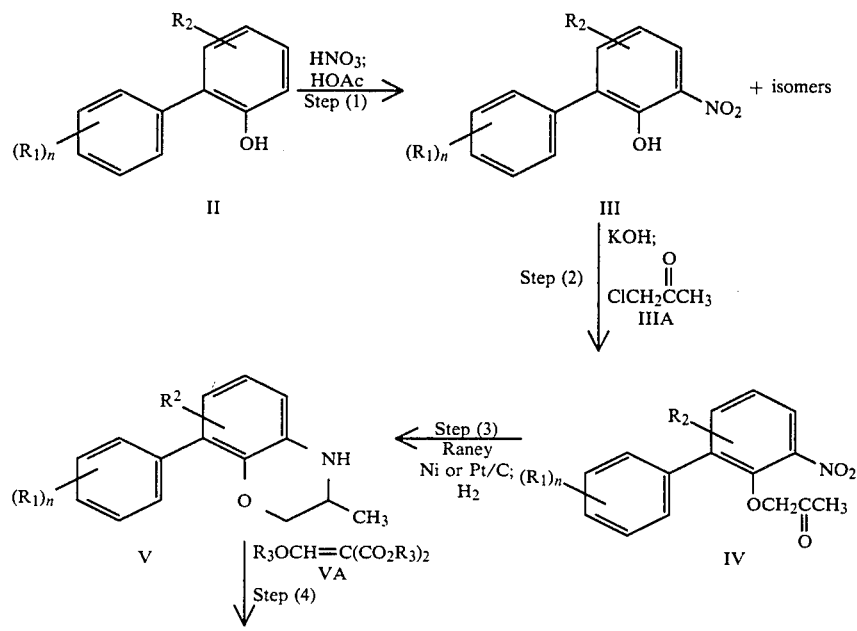

-continued
REACTION SCHEME I

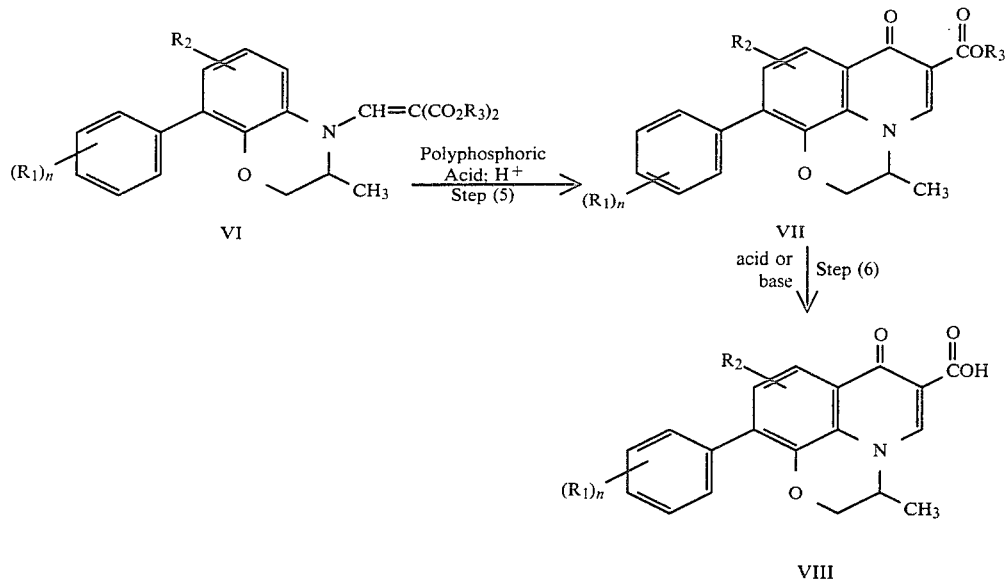

wherein $R_1$, n, and $R_2$ are defined as indicated previously and each $R_3$ is independently lower alkyl.

In step (1) of Reaction Scheme 1, a 2-hydroxybiphenyl of Formula II is nitrated using nitric acid in the presence of acetic acid to provide a 2-hydroxy-3-nitrobiphenyl of Formula III. A preferred method of carrying out this reaction is as follows. The biphenyl of Formula II is dissolved in glacial acetic acid at a temperature of 15° to 20° C. Concentrated nitric acid is then added thereto and the resulting mixture is stirred for a short period of time (usually less than about one hour). Thereafter the mixture is diluted with an equal volume of water. The 2-hydroxy-3-nitrobiphenyl of Formula III is separated from the mixture, usually as an oil, and is triturated with hot hexane and purified by chromatography. As an alternative to conducting step (1), known 2-hydroxy-3-nitrobiphenyls may be employed directly in step (2) below.

The novel compounds of Formula IV are prepared in step (2) by forming a salt of the phenolic group of the 2-hydroxy-3-nitrobiphenyl of Formula III and reacting this salt with an alpha-haloacetone such as the illustrated alpha-chloroacetone of Formula IIIA. Salts are formed by reacting the phenolic group with a base, for example, with an alkali metal or alkaline earth hydroxide such as sodium or potassium hydroxide. These salts are novel and may be isolated as brightly colored (e.g., red) crystalline solids. The salts are partially or completely dissolved in a strongly polar solvent such as N,N-dimethylformamide. An equimolar amount of an alkali metal halide salt such as sodium or potassium iodide is then added, followed by the addition of the alpha-haloacetone. This reaction is carried out at moderate temperatures, e.g. 20° to 60° C. The product of Formula IV is isolated readily by conventional methods such as extraction and chromatography.

In step (3), the compound of Formula IV is cyclized reductively to provide a novel benzoxazine of Formula V. The reductive cyclization is carried out catalytically with hydrogen gas in the presence of a catalyst such as Raney nickel or platinum on carbon. A non-reactive solvent such as ethanol is used. Moderate temperatures from 0° to 50° C. are generally sufficient to achieve an adequate rate of reaction, although higher temperatures may be used.

The benzoxazine of Formula V is then reacted in step (4) with an equimolar amount of a diester of an alkoxymethylenemalonic acid. The preferred diesters are the illustrated dialkyl alkoxymethylenemalonates of Formula VA such as diethyl ethoxymethylenemalonate. However, other suitable diesters of an alkoxymethylenemalonic acid such as N-cycloisopropylidenyl alkoxymalonates (e.g., N-cycloisopropylidenyl ethoxymalonate) may be employed. The condensation reaction is generally carried out in the absence of solvent at a temperature of 100° to 200° C., and preferably at 130° to 150° C., for several hours. The progress of the reaction may be followed by chromatography until all starting material has reacted. The novel product of Formula VI may, if desired, be isolated and purified prior to conducting step (5).

In step (5), polyphosphoric acid is added to the intermediate of Formula VI and the mixture is heated at a temperature of about 100° to 140° C. to provide an ester of Formula VII by a condensation reaction.

In step (6) the ester of Formula VII is hydrolyzed to the free acid of Formula VIII with strong acid, e.g., hydrochloric acid, or with base, e.g., sodium hydroxide.

Preparation of the quinolizines of Formula I may be carried out as illustrated in Reaction Scheme II below:

REACTION SCHEME II

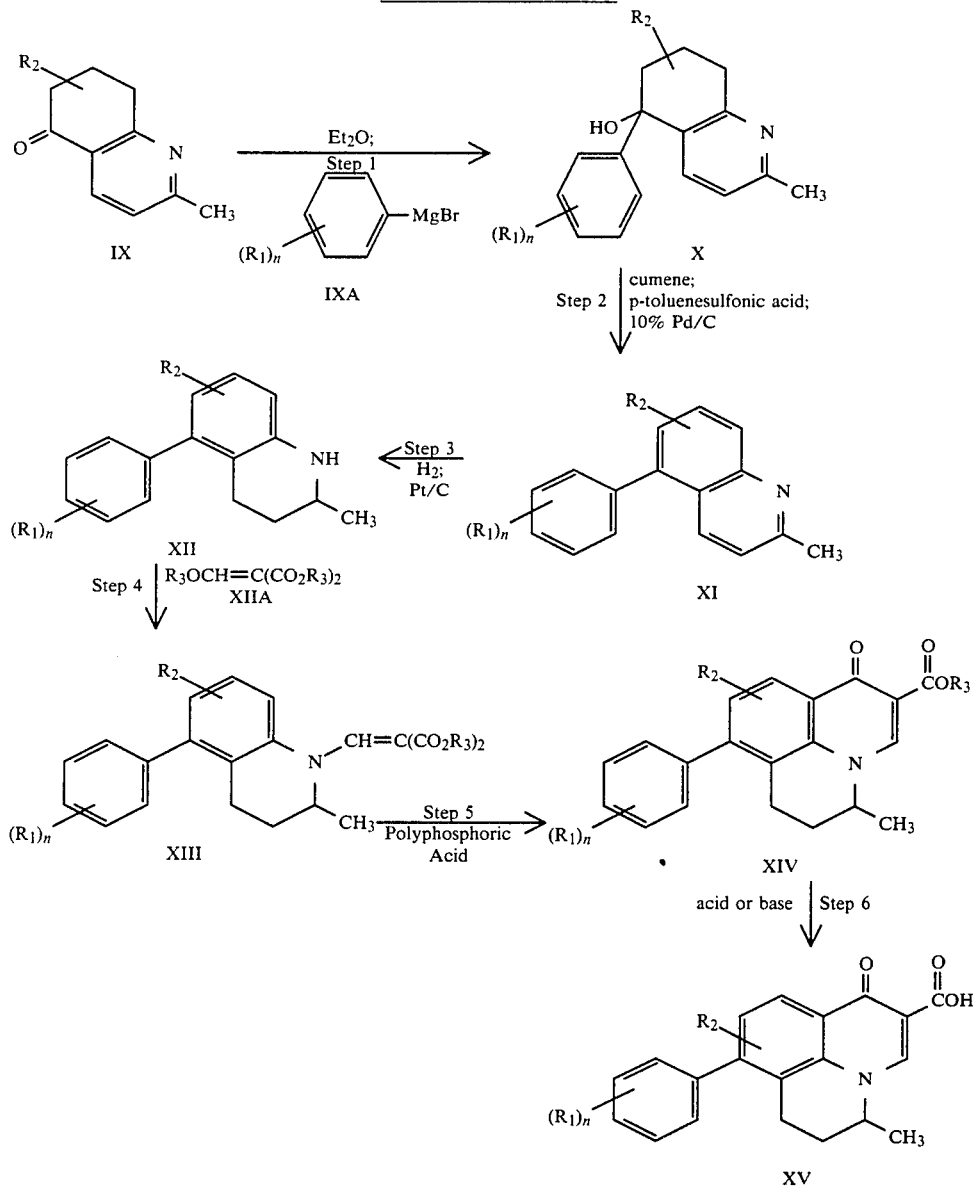

wherein $R_1$, n, $R_2$ and $R_3$ are defined as indicated previously.

In step (1) the compound of Formula IX is reacted with a known optionally substituted phenylmagnesium bromide IXA in a conventional Grignard reaction. The novel product of Formula X is readily isolated as a solid.

The compound of Formula X is dehydrated and aromatized in step (2) to provide the novel optionally substituted 5-phenylquinaldine of Formula XI. This reaction is carried out at a reflux temperature in a high boiling aromatic solvent such as cumene and in the presence of p-toluenesulfonic acid and 10% palladium on carbon. The progress of the reaction may be followed by chromatography. The p-toluenesulfonic acid is used at a level of less than 20 weight percent (based on the compound of Formula X), and preferably is used at about 5 weight percent. The palladium on carbon is used at a level of up to 40 weight percent (based on the compound of Formula X), and preferably is used at 10 to 30 weight percent. The 5-phenylquinaldine of Formula XI may be isolated as a solid or used directly in Step 3 without further purification.

The 5-phenylquinaldine of Formula XI is reduced in step (3) to provide a novel optionally substituted 5-phenyltetrahydroquinaldine of Formula XII. The reduction is carried out catalytically in the presence of hydrogen in a suitable non-reactive solvent such as ethanol. The preferred catalyst is platinum on carbon.

In step (4) the compound of Formula XII is reacted with a dialkyl alkoxymethylenemalonate of Formula XIIA in the same manner as described in step (4) in Scheme I. The procedure is analogous to that of step 4 of Scheme I.

In step (5), polyphosphoric acid is added to the intermediate of Formula XIII and heated in accordance with the procedure of step (5) of Reaction Scheme I to provide the ester of Formula XIV.

In step (6), the ester of Formula XIV is hydrolyzed to the free acid of Formula XV with a strong acid or base.

Reaction Scheme III illustrates the preparation of the quinoxalines of Formula I.

In step (3) the intermediate of Formula XVIII is condensed with an alpha-keto acid such as illustrated pyruvic acid (Formula XVIIIA) to provide a novel intermediate of Formula XIX.

SCHEME III

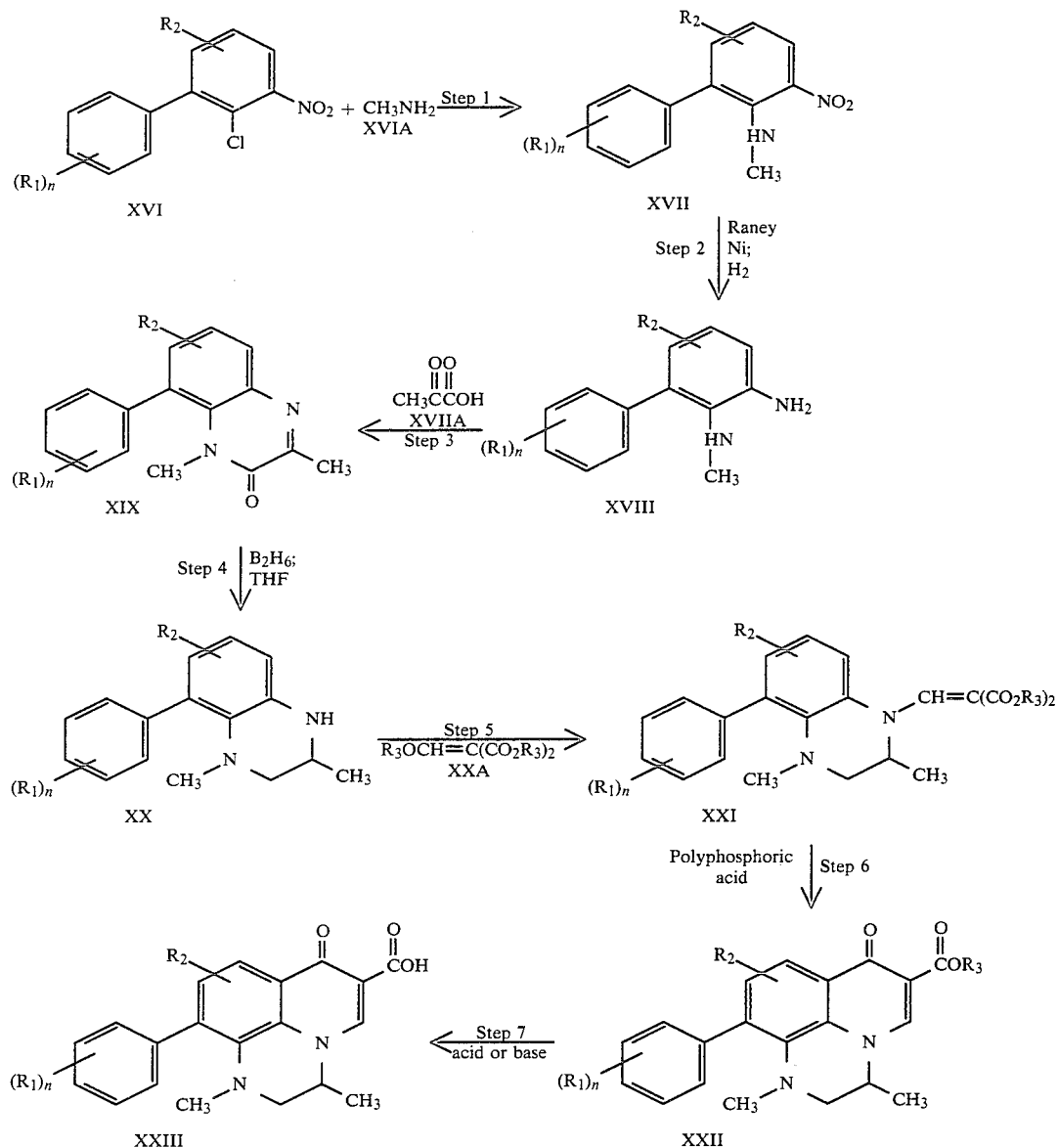

wherein $R_1$, n, $R_2$, and $R_3$ are as defined previously.

The starting materials are known or readily prepared optionally substituted 2-chloro-3-nitrobiphenyls of Formula XVI. In step (1) the reactive chlorine is replaced by conventional reaction with methylamine of Formula XVIA to provide an intermediate of Formula XVII.

In step (2) the nitro group of the intermediate of Formula XVII is reduced catalytically to provide a diamine of Formula XVIII. The catalyst is preferably Raney nickel.

In step (4) the novel intermediate of Formula XIX is reduced to a novel phenylquinoxaline of Formula XX using diborane and a suitable solvent such as tetrahydrofuran.

Steps 5, 6 and 7 are carried out as described for steps 4, 5, and 6 in Reaction Schemes I and II to provide intermediates of Formulas XXI and XXII and the final product of Formula XXIII, respectively.

Reaction Scheme IV illustrated below is directly analogous to Scheme II and describes the preparation of the pyrroloquinolines of the present invention.

REACTION SCHEME IV

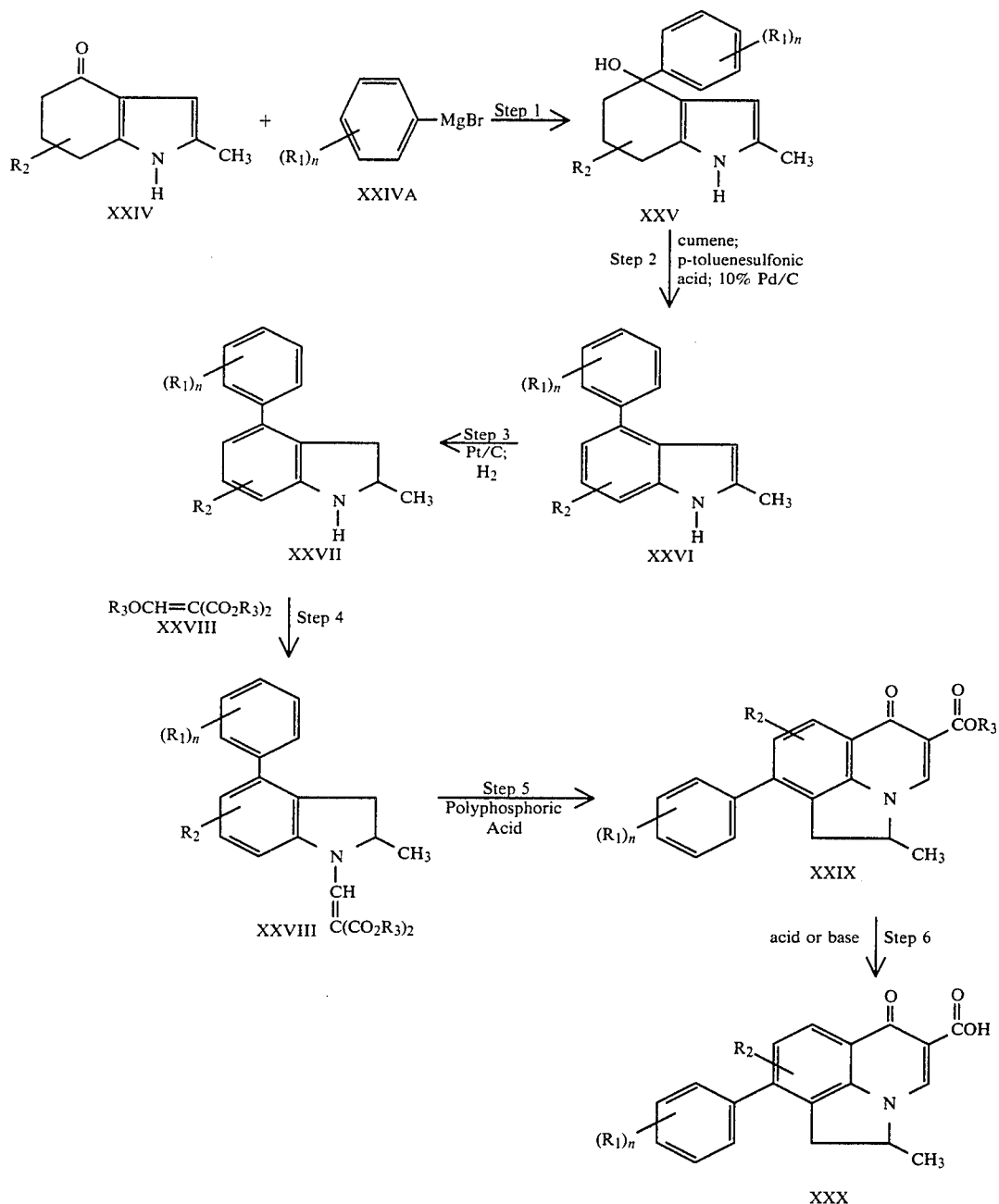

wherein $R_1$, n, $R_2$ and $R_3$ are as defined previously.

The starting materials for preparing the pyrroloquinolines of the present invention are the known compounds of Formula XXIV. Steps 1-6 of Reaction Scheme IV are conducted in accordance with the procedures stated above in connection with the respective Steps 1-6 of Reaction Scheme II.

The invention may be further illustrated by reference to the following non-limiting examples.

Preferred compounds of the invention due to their potency and broad spectrum of activity are the compounds of Examples 1, 2, 15, 16, 17, 19, 20, 22, 23, 25, 26, 28, 29 and 30.

EXAMPLE 1

Preparation of 2,3-Dihydro-3-methyl-7-oxo-10-phenyl-7H-pyrido[1,2,3-d,e]-1,4-benzoxazine-6-carboxylic Acid Part A. Preparation of alpha-(2-Nitro-6-phenylphenoxy)acetone A solution of 9.8 g (0.175 mole) of potassium hydroxide in 75 ml of ethanol was added to a solution of 18.8 g of the known compound 2-hydroxy-3-nitrobiphenyl in 75 ml of ethanol. The solution was cooled for 16 hours. The intermediate obtained, the potassium salt of the phenolic group, was separated by filtration as bright red crystals and washed with hexane. These crystals were dissolved in 75 ml of N,N-dimethylformamide and 1.3 g (8.74 mmole) of sodium iodide was added to the resulting solution. To this solution was added 7 ml (0.0874 mole) of chloroacetone while maintaining the temperature at 40° to 50° C. After two hours the solution was poured into 250 ml of water. This solution was extracted with four 75 ml portions of diethyl ether. The ether extracts were washed twice with 100 ml portions of water, then dried over magnesium sulfate. The solvent was evaporated to provide 18.2 g (77%) of a yellow oil. Infrared spectral analysis indicated that the product was alpha-(2-nitro-6-phenylphenoxy)acetone.

Part. B. Preparation of
3,4-Dihydro-5-phenyl-2H-1,4-benzoxazine

A solution of 5.7 g (0.021 mole) of alpha-(2-nitro-6-phenylphenoxy)acetone in 350 ml of ethanol was hydrogenated using 1.5 g of 5% platinum on charcoal as the catalyst. A Paar apparatus was employed using 50 psi of hydrogen and hydrogenation reaction was allowed to proceed for 30 minutes. The reaction mixture was filtered through celite and the solvent was then removed by evaporation to provide 4.3 g (91%) of 3,4-dihydro-5-phenyl-2H-1,4-benzoxazine as a dark liquid. The infrared spectrum of the product was consistent with the assigned structure.

Part C. Preparation of Ethyl
2,3-Dihydro-3-methyl-7-oxo-10-phenyl-7H-pyrido[1,2,3-de]-1,4-benzoxazine-6-carboxylate A mixture of 9.9 g of 3,4-dihydro-5-phenyl-2H-1,4-benzoxazine and 19.8 g of diethyl ethoxymethylenemalonate was heated at 140° C. for 2.5 hours. Analysis by thin layer chromatography indicated that all of the starting material had been converted to diethyl 2-[N-(3,4-dihydro-5-phenyl-2H-1,4-benzoxazinyl)]methylenemalonate. To this mixture was added 50 g of polyphosphoric acid without additional heating. After the exotherm had ceased the mixture was heated at 100° C. for 0.5 hour. The thick mixture was then poured into 300 ml of stirred water, which was then filtered to provide a dark solid. The solid was recrystallized from ethanol to provide white fluffy solid ethyl 2,3-dihydro-3-methyl-7-oxo-10-phenyl-7H-pyrido-[1,2,3-de]-1,4-benzoxazine-6-carboxylate, m.p. 246° C. Analysis: Calculated for $C_{21}H_{19}NO_4$: %C, 72.2; %H, 5.5; %N, 4.0; Found: %C, 71.8; %H, 5.1; %N, 3.6. The structural assignment was confirmed by infrared spectral analysis.

Part. D. Preparation of
2,3-Dihydro-3-methyl-7-oxo-10-phenyl-7H-pyrido[1,2,3-de]-1,4-benzoxazine-6-carboxylic Acid A mixture of 11.5 g of ethyl 2,3-dihydro-3-methyl-7-oxo-10-phenyl-7H-pyrido[1,2,3-de]-1,4-benzoxazine-6-carboxylate and 75 ml of glacial acetic acid was heated to reflux temperature and 75 ml of 6N hydrochloric acid was subsequently added. Refluxing was continued for one hour after which time 150 ml of water was added. The solution was cooled and filtered to provide light brown solid 2,3-dihydro-3-methyl-7-oxo-10-phenyl-7H-pyrido[1,2,3-de]-1,4-benzoxazine-6-carboxylic acid, m.p. 295°–296° C. Recrystallization from aqueous N,N-dimethylformamide gave light yellow crystals. Analysis: Calculated for $C_{19}H_{15}NO_4$: %C, 71.0; %H, 4.7; %N, 4.4; Found: %C, 70.4; %H, 4.6; %N, 4.3. The structural assignment was confirmed by infrared and nuclear magnetic resonance spectral analyses.

Part E. Preparation of Sodium
2,3-Dihydro-3-methyl-7-oxo-10-phenyl-7H-pyrido[1,2,3-de]-1,4-benzoxazine-6-carboxylate To a solution of 0.0997 g of sodium hydroxide in 40 ml of water was added 0.8 g of 2,3-dihydro-3-methyl-7-oxo-10-phenyl-7H-pyrido[1,2,3-de]-1,4-benzoxazine-6-carboxylic acid. The mixture was heated briefly until the carboxylic acid dissolved. The solution was then filtered and the filtrate obtained was then evaporated to provide a residue. The residue was dissolved in 50 ml of water, the solution filtered and the filtrate was lyophilized to provide light tan solid, sodium, 2,3-dihydro-3-methyl-7-oxo-10-phenyl-7H-pyrido[1,2,3-de]-1,4-benzoxazine-6-carboxylate, m.p. 236° C. (dec.). Analysis: Calculated for $C_{19}H_{14}NNaO_4 \cdot 1.5H_2O$: %C, 61.6; %H, 4.6; %N, 3.8; Fo und: %C, 61.4; %H, 4.3; %N, 3.6. The structural assignment was confirmed by infrared spectral analysis.

EXAMPLE 2

Preparation of
6,7-Dihydro-5-methyl-1-oxo-8-phenyl-1H,5H-benzo[ij]-quinolizine-2-carboxylic Acid Part A. Preparation of
5-Hydroxy-5-phenyl-5,6,7,8-tetrahydroquinaldine To a stirred solution of 0.155 moles of phenylmagnesium bromide in 250 ml of diethyl ether was added dropwise a solution of 2.0 g (0.124 mole) of 5-keto-5,6,7,8-tetrahydroquinaldine in 100 ml of diethyl ether. After all of the tetrahydroquinaldine had been added the mixture was then treated with an excess of a saturated aqueous ammonium chloride solution. The ether layer was separated, dried and evaporated to prevent a residue. This residue was dissolved in dilute hydrochloric acid and the aqueous acid layer was then extracted sequentially with diethyl ether and hexane. The acid layer was then basified with aqueous sodium hydroxide. Filtration provided yellow solid 5-hydroxy-5-phenyl-5,6,7,8-tetrahydroquinaldine, which had a m.p. of 130°–134° C. after recrystallization from a dichloromethane-hexane mixture. Analysis: Calculated for $C_{16}H_{17}NO$: %C, 80.3; %H, 7.2; %N, 5.9; Found: %C, 80.2; %H, 7.2; %N, 5.5. The structural assignment was confirmed by infrared and nuclear magnetic resonance spectral analyses.

Part B. Preparation of 5-Phenylquinaldine

A mixture of 20 g (0.084 mole) of 5-hydroxy-5-phenyl-5,6,7,8-tetrahydroquinaldine, 10 g of 10% palladium on carbon, 2.3 g of para-toluenesulfonic acid and 200 ml of cumene was heated at its reflux temperature for 24 hours. The mixture was filtered hot, and then the filtrate was evaporated to provide a residue. This residue was dissolved in dilute hydrochloric acid. This solution was extracted with diethyl ether and the acid layer was then neutralized with 50% aqueous sodium hydroxide solution. The product was extracted into diethyl ether. The organic layer was dried and then evaporated to provide a solid residue. Recrystallization from methanol provided white crystals of 5-phenylquinaldine. Analysis: Calculated for $C_{16}H_{13}N \cdot H_2O$: %C, 81.0; %H, 6.4; %N, 5.8; Found: %C, 81.4; %H, 6.6; %N, 5.5. The structure assignment was confirmed by nuclear magnetic resonance spectral analysis.

Part C. Preparation of 5-Phenyl-1,2,3,4-tetrahydroquinaldine

To a solution of 5.5 g (0.025 mole) of 5-phenylquinaldine in 80 ml of ethanol and 5 ml of glacial acetic acid, about 2 g of 5% platinum on carbon was added and the mixture was hydrogenated on a Paar apparatus at about 34 psi of hydrogen. Hydrogen uptake stopped at 70 lb. (90 lb. theoretical). The mixture was filtered, the ethanol was removed by evaporation in vacuo and 25 ml of water was added. The mixture was basified with 50% aqueous sodium hydroxide and the resulting mixture was then extracted with diethyl ether. The organic layer was dried and the solvent evaporated to provide 5.3 g of an oil. Nuclear magnetic resonance and infrared spectral analyses of the product showed it to be the desired product, 5-phenyl-1,2,3,4-tetrahydroquinaldine.

Part D. Preparation of Ethyl (5-Phenyl-1,2,3,4-tetrahydroquinaldinyl)methylenemalonate A mixture of 5.2 g (0.023 mole) of 5-phenyl-1,2,3,4-tetrahydroquinaldine (the product of Part C) and 7.6 g (0.035 mole) of diethyl ethoxymethylenemalonate in 100 ml of xylene was heated at its reflux temperature for 24 hours. The mixture was cooled and the solvent was then removed by evaporation in vacuo to provide the desired product as an oil.

Part E. Preparation of Ethyl 6,7-Dihydro-5-methyl-1-oxo-8-phenyl-1H,5H-benzo[ij]-quinolizine-2-carboxylate To the product of Part D was added with stirring 25 g of polyphosphoric acid. The mixture was heated on a steam bath for one hour, at which time 400 ml of water was added. The mixture was stirred until a solid product precipitated. The solid was separated by filtration to provide 6.5 g of ethyl 6,7-dihydro-5-methyl-1-oxo-8-phenyl-1H,5H-benzo[ij]quinolizine-2-carboxylate. Infrared spectral analysis confirmed this structural assignment. The melting point after recrystallization once from methanol was 198° C.

Part F. Preparation of 6,7-Dihydro-5-methyl-1-oxo-8-phenyl-1H,5H-benzo[ij]-quinolizine-2-carboxylic Acid A solution of 2.0 g of ethyl 6,7-dihydro-5-methyl-1-oxo-8-phenyl-1H,5H-benzo[ij]quinolizine-2-carboxylate in concentrated hydrochloric acid was prepared and heated at its reflux temperature for 10 minutes. Water was then added and the solid precipitate was obtained by filtration, washed with water and methanol and dried to provide white solid 6,7-dihydro-5-methyl-1-oxo-8-phenyl-1H,5H-benzo[ij]quinolizine-2-carboxylate acid, m.p. 238–241 C. Analysis: Calculated for $C_{20}H_{17}NO_3$: %C, 75.2; %H, 5.4, %N, 4.4; Found: %C, 74.9; %H, 5.2; %N, 3.9. The structural assignment was confirmed by infrared and nuclear magnetic resonance spectral analyses.

EXAMPLE 3–5

Using the method of Example 2, Part A, the following intermediates were prepared (Table I):

TABLE 1

| Example No. | Starting Materials | Intermediate of Formula X (Reaction Scheme II) | Analysis |
|---|---|---|---|
| 3 | 5-keto-5,6,7,8-tetrahydroquinaldine and 3,4-dimethoxyphenyl magnesium bromide | [structure] | $C_{18}H_{21}NO_3 \cdot H_2O$ 67.4% C; 7.2% H; 4.2% N 67.4% C; 7.3% H; 4.4% N |
| 4 | 5-keto-5,6,7,8-tetrahydroquinaldine and 4-methoxyphenyl-magnesium bromide | [structure] | white solid |
| 5 | 5-keto-7-methyl-5,6,7,8-tetrahydroquinaldine and phenyl magnesium bromide | [structure] | yellow-colored solid; infrared and nuclear magnetic resonance spectra confirmed structure |

EXAMPLES 6–8

Using the method of Example 2, Parts B and C, the following intermediates were prepared (Table 2):

TABLE 2

| Example No. | Starting Material (Intermediate of Formula X) | Intermediate of Formula XI (Reaction Scheme II) | Intermediate of Formula XII (Reaction Scheme II) |
|---|---|---|---|
| 6 | See Example 3 | [structure: 2-methylquinoline with 3,4-dimethoxyphenyl substituent] solid; nuclear magnetic resonance spectrum confirmed structural assignment | [structure: corresponding 1,2,3,4-tetrahydroquinoline] |
| 7 | See Example 4 | [structure: 2-methylquinoline with 4-methoxyphenyl substituent] light green-colored solid; m.p. 120–123 C.; $C_{17}H_{15}NO$; 81.9% C; 6.1% H; 5.6% N / 81.9% C; 6.1% H; 5.4% N | [structure: corresponding tetrahydroquinoline] infrared and nuclear magnetic resonance spectra confirmed structural assignment |
| 8 | See Example 5 | [structure: 2,7-dimethyl-5-phenylquinoline] solid | [structure: corresponding tetrahydroquinoline] nuclear magnetic resonance and infrared spectra confirmed structural assignment |

EXAMPLES 9–11

Using the method of Example 2, Part D, the following intermediates were prepared (Table 3):

TABLE 3

| Example No. | Starting Material of Formula XII | Intermediate of Formula XIII wherein Alk is ET(ethyl) (Reaction Scheme II) | Ethyl Ester Intermediate of Formula I |
|---|---|---|---|
| 9 | Example 6 | [structure with $CH=CH(CO_2Et)_2$ group] | [structure] yellow solid; infrared and nuclear magnetic resonance spectra confirmed structural assignment |

TABLE 3-continued

| Example No. | Starting Material of Formula XII | Intermediate of Formula XIII wherein Alk is ET(ethyl) (Reaction Scheme II) | Ethyl Ester Intermediate of Formula I |
|---|---|---|---|
| 10 | Example 7 | [structure: tetrahydroquinoline with CH=C(CO2Et)2 on N, CH3 substituent, linked to 4-methoxyphenyl] | [structure: benzo[ij]quinolizine with 4-methoxyphenyl, COCH2CH3, CH3] |
| 11 | Example 8 | [structure: H3C-substituted tetrahydroquinoline with CH=C(CO2Et)2 on N, CH3, phenyl] | [structure: benzo[ij]quinolizine with CH3, phenyl, COCH2CH3, CH3] — infrared spectrum confirmed structural assignment |

EXAMPLES 12–14

Using the method of Example 2, Part E, the following compounds of Formula I were prepared (Table 4):

EXAMPLE 15

A mixture of 2.5 g (6.6 mmole) of ethyl 6,7-dihydro-8-(4-methoxyphenyl)-1-oxo-1H,5H-benzo[ij]quinolizine-2-carboxylate and 50 ml of 48% hydrobromic acid was heated at its reflux temperature for 1.5 hours. Water was

TABLE 4

| Example No. | Ethyl Ester Intermediate of Formula I | Product of Formula I | Analysis |
|---|---|---|---|
| 12 | Example 9 | [structure: benzo[ij]quinolizine with 3,4-dimethoxyphenyl, COOH, CH3] | m.p. >250° C.; $C_{22}H_{21}NO_5 \cdot 0.5\ H_2O$ 68.0% C; 5.7% H; 3.6% N; 68.2% C; 5.6% H; 3.5% N |
| 13 | Example 10 | [structure: benzo[ij]quinolizine with 4-methoxyphenyl, COOH, CH3] | m.p. 246–250° C.; $C_{21}H_{19}NO_4$; 72.2% C; 5.5% H; 4.0% N; 72.1% C; 5.4% H; 4.0% N |
| 14 | Example 11 | [structure: benzo[ij]quinolizine with CH3, phenyl, COOH, CH3] | m.p. >200° C.; $C_{21}H_{19}NO_3 \cdot 0.5\ H_2O$; 73.6% C; 5.8% H; 4.1% N; 73.5% C; 5.7% H; 4.0% N | added to precipitate 6,7-Dihydro-8-(4-hydroxyphenyl)-1-oxo-1H,5H-benzo[ij]quinolizine-2-carboxylic acid, m.p. >270° C., as a golden-brown solid. Recrystallization was carried out using aqueous N,N-dimethylformamide. Analysis: Calculated for $C_{20}H_{17}NO_4.H_2O$: %C, 68.0; %H, 5.4; %N, 3.9; Found: %C, 68.3; %H, 5.1 %N, 3.7. The structural assignment was confirmed by infrared and nuclear magnetic resonance spectral analyses.

EXAMPLE 16

A sample of 6,7-dihydro-1-oxo-8-phenyl-1H,5H-benzo[ij]quinolizine-2-carboxylic acid, 100 ml of water and 0.176 g of sodium hydroxide was heated to obtain solution, filtered, then lyophilized to provide fluffy white solid sodium 6,7-dihydro-1-oxo-8-phenyl-1H,5H-benzo[ij]qunilozine-2-carboxylate, m.p. 230–231° C. Analysis: Calculated for $C_{20}H_{16}NNaO_3.1.5\ H_2O$: %C, 65.2; %H, 5.2; %N, 3.8; Found: %C, 65.1; %H, 4.8; %N, 3.6. The structural assignment was confirmed by infrared spectral analysis.

EXAMPLE 17

To a cold (0° to 5° C.), stirred solution of 90% nitric acid was added, in small portions, 2.0 g (9.4 mmole) of 2,3-dihydro-3-methyl-7-oxo-10-phenyl-7H-pyrido[1,2,3-de]-1,4-benzoxazine-6-carboxylic acid. As the result of this addition, the mixture warmed to about 10° C. The mixture was cooled with an icebath and stirred at 0° to 5° C. for one hour. The solution was poured into 125 ml of water and the resulting mixture was stirred for 15 minutes and filtered to provide a tan solid. Recrystallization from N,N-dimethylformamide provided 2,3-dihydro-3-methyl-8-nitro-10-(4-nitrophenyl)-7-oxo-7H-pyrido[1,2,3-de]-1,4-benzoxazine-6-carboxylic acid, m.p. 290°–292° C. (dec.). Analysis: Calculated for $C_{19}H_{13}N_3O_8$: %C, 55.5; %H, 3.2; %N, 10.2; Found: %C, 55.0; %H, 2.7; %N, 10.5. The structural assignment was confirmed by infrared and nuclear magnetic resonance spectral analyses.

EXAMPLE 18

To a stirred, cold (5° C.) 400 ml portion of 90% nitric acid was added 2.3 g of 6,7-dihydro-5-methyl-1-oxo-8-phenyl-1H,5H-benzo[ij]quinolizine-2-carboxlic acid. The solution was stirred at 5°–10° C. for one hour, then diluted with 1.5 liters of ice-water. The solid was evaporated by filtration and dried to provide 6,7-dihydro-5-methyl-8-(4-nitrophenyl)-1-oxo-1H,5H-benzo[ij]quinolizine-2-carboxylic acid, m.p. >300° C. Analysis: Calculated for $C_{20}H_{16}N_2O_5$: %C, 65.9; %H, 4.4; %N, 7.7; Found: %C, 65.3; %H, 4.6; %N, 7.4. The structural assignment was confirmed by infrared and nuclear magnetic resonance spectral analyses.

EXAMPLE 19

To a solution of 6.4 g (17.6 mmole) of 6,7-dihydro-5-methyl-8-(4-nitrophenyl)-1-oxo-1H,5H-benzo[ij]quinolizine-2-carboxylic acid in 100 ml of trifluroacetic acid was added 1.0 g of 10% palladium on carbon. The mixture was hydrogenated on a Paar apparatus at 50 psi. The theoretical amount of hydrogen (92 psi) was absorbed. The mixture was filtered and then evaporated in vacuo to provide 25 ml of solution which was basified with 10% sodium hydroxide solution. The resulting mixture was filtered to isolate the solid product. Recrystallization from aqueous N,N-dimethylformamide provided yellow crystals of 8-(4-aminophenyl)-6,7-dihydro-5-methyl-1-oxo-1H,5H-benzo[ij]quinolizine-2-carboxylic acid as the hydrate, m.p. 246°–247° C. Analysis: Calculated for $C_{20}H_{18}N_2O_3.0.5\ H_2O$: %C, 69.9; %H, 5.3; %N, 8.1; Found: %C, 69.9; %H, 5.4; %N, 8.1. The structural assignment was confirmed by infrared and nuclear magnetic resonance spectral analyses.

EXAMPLE 20

To a solution of 1.0 g (3.0 mmole) of 8-(4-aminophenyl)-6,7-dihydro-5-methyl-1-oxo-1H,5H-benzo[ij]quinolizine-2-carboxylic acid in 20 ml of hot acetic acid was added 1.0 g of 2,5-dimethoxytetrahydrofuran. The solution was heated at its reflux temperature for 30 minutes. Water was added to the solution until the solution became cloudly. The solution was cooled and the solid was separated by filtration and recrystallized from aqueous N,N-dimethylformamide. The product obtained was 6,7-dihydro-5-methyl-1-oxo-8-(4-N-pyrryl)-phenyl-1H,5H-benzo[ij]quinolizine-2-carboxylic acid hydrate, m.p. 189°–190° C. (dec.). Analysis: Calculated for $C_{24}H_{20}N_2O_3.0.75\ H_2O$: %C, 72.4; %H, 5.4; %N, 7.0; Found: %C, 72.4; %H, 5.3; %N, 7.2. The structural assignment was confirmed by infrared and nuclear magnetic resonance spectral analyses.

EXAMPLE 21

A solution of 1.5 g (4.5 mmole) of 8-(4-aminophenyl)-6,7-dihydro-5-methyl-1-oxo-1H,5H-benzo[ij]quinolizine-2-carboxylic acid in 40 ml of concentrated hydrochloric acid was cooled to about 5° C. To this solution was added over ten minutes 1.7 ml (5 mmole) of a 20% aqueous sodium nitrite solution. After stirring for 10 additional minutes, 0.15 g of copper bronze was added. The solution was stirred for 1.5 hours and heated on a steam bath for 15 minutes. The solution was then poured into 100 ml of stirred water. The solid was separated by filtration and recrystallized from aqueous N,N-dimethylformamide. The product was tan crystals of 8-(4-chlorophenyl)-6,7-dihydro-5-methyl-1-oxo-1H,5H-benzo[ij]quinolizine-2-carboxylic acid, m.p. 248°–249° C. Analysis: Calculated for $C_{20}H_{16}ClNO_3$: %C, 67.9; %H, 4.6; %N, 4.0; Found: %C, 68.2; %H, 4.9; %N, 4.5. The structural assignment was confirmed by infrared and nuclear magentic resonance spectral analyses.

EXAMPLE 22

A mixture of 0.7 g (2.1 mmole) of 8-(4-aminophenyl)-6,7-dihydro-5-methyl-1-oxo-1H,5H-benzo[ij]quinolizine-2-carboxylic acid, 5 ml of acetic acid and 2.5 ml of acetic anhydride was heated at its reflux temperature until solid was observed to precipitate. The mixture was diluted with 10 ml of water, stirred and cooled. The product was separated by filtration to provide 8-(4-acetamidophenyl)-6,7-dihydro-5-methyl-1-oxo-1H,5H-benzo[ij]quinolizine-2-carboxylic acid hydrate, m.p. 168°–170° C. Analysis: Calculated for $C_{22}H_{20}N_2O_4.0.75\ H_2O$: %C, 67.8; %H, 5.6; %N, 7.2; Found: %C, 67.9; %H, 5.3; %N, 7.4. The structural assignment was confirmed by infrared and nuclear magnetic resonance spectral analyses.

EXAMPLE 23

A solution of 0.9 g (2.7 mmole) of 8-(4-aminophenyl)-6,7-dihydro-5-methyl-1-oxo-1H,5H-benzo[ij]quinolizine-2-carboxylic acid in 45 ml of 96% formic acid and 3 ml of 37% formaldehyde was hydrogenated on a Paar apparatus in the presence of about 1 g of palladium on carbon at 50 psi and at 50° C. for 72 hours. The solution was filtered, then evaporated to about 20 ml. This solution was diluted with 20 ml of water, then evaporated to about 10 ml. This solution was diluted first with 10 ml of N,N-dimethylformamide, then with 20 ml of water. The product was 6,7-dihydro-8-[4-(N,N-dimethylamino)-phenyl]-5-methyl-1-oxo-1H,5H-benzo[ij]quinolizine-2-carboxylic acid hydrate, m.p. 257°–259° C. Analysis: Calculated for $C_{22}H_{22}N_2O_3 \cdot \frac{1}{3} H_2O$: %C, 71.7; %H, 6.2; %N, 7.6; Found: %C, 71.5; %H, 6.3; %N, 8.0. The structural assignment was confirmed by infrared and nuclear magnetic resonance spectral analyses.

EXAMPLE 24

To a 0.8 g sample of 8-(4-aminophenyl)-6,7-dihydro-5-methyl-1-oxo-1H,5H-benzo[ij]quinolizine-2-carboxylic acid in 5 ml of hot acetic acid was added dropwise 0.3 ml of chloroacetyl chloride. The resulting solution was cooled and stirred for 20 minutes and then filtered. The solid was dried to provide golden crystals of 8-(4-chloroacetamidophenyl)-6,7-dihydro-5-methyl-1-oxo-1H,5H-benzo[ij]quinolizine-2-carboxylic acid hydrate, m.p. 297° C. Analysis: Calculated for $C_{22}H_{19}N_2O_4Cl \cdot 0.5 H_2O$: %C, 63.4; %H, 4.6; %N, 6.7; Found: %C, 62.9; %H, 4.8; %N, 6.7. The structural assignment was confirmed by infrared and nuclear magnetic resonance spectral analyses.

EXAMPLE 25

To a hot mixture of 20 ml of 97% formic acid and 10 ml of acetic anhydride was added 1.5 g of 8-(4-aminophenyl)-6,7-dihydro-5-methyl-1-oxo-1H,5H-benzo[ij]quinolizine-2-carboxylic acid. The mixture was heated on a steam bath for 15 minutes and then evaporated. The residue was triturated with water to provide a solid. The solid was recrystallized from glacial acetic acid to provide 6,7-dihydro-8-(4-formamidophenyl)-5-methyl-1-oxo-1H,5H-benzo[ij]quinolizine-2-carboxylic acid hydrate, m.p. >300° C. Analysis: Calculated for $C_{21}H_{18}N_2O_4 \cdot \frac{1}{3} H_2O$: %C, 68.5; %H, 5.1; %N, 7.6; Found: %C, 68.8; %H, 5.2; %N, 7.6 The structural assignment was confirmed by infrared and nuclear magnetic resonance spectral analyses.

EXAMPLE 26

To a cold (5° C.) solution of 1.5 g of 8-(4-aminophenyl)-6,7-dihydro-5-methyl-1-oxo-1H,5H-benzo[ij]quinolizine-2-carboxylate acid in 40 ml of 48% hydrobromic acid was added over three minutes, 1.7 ml of 20% aqueous sodium nitrite solution. The mixture was stirred at 5° C., for 15 minutes followed by the addition of 0.15 g of copper bronze thereto. Stirring was continued for about two hours at about 20° C. subsequently mixture was heated on a steam bath for about 0.5 hour. The mixture was then decanted into stirred water and the resulting solid was isolated by filtration and dried. Recrystallization from aqueous N,N-dimethylformamide twice provided 8-(4-bromophenyl)-6,7-dihydro-5-methyl-1-oxo-1H,5H-benzo[ij]quinolizine-2-carboxylic acid, m.p. 263°–265° C. Analysis: Calculated for $C_{20}H_{16}BrNO_3 \cdot 0.9 H_2O$: %C, 57.9; %H, 4.2; %N, 3.4; Found: %C, 57.4; %H, 3.7; %N, 3.6. The structural assignment was confirmed by infrared and nuclear magnetic resonance spectral analyses.

EXAMPLES 27–30

Using the method described in Reaction Scheme III, Step 1, and starting with the indicated 2-chloro-3-nitrobiphenyls, the following compounds of Formula XVII may be prepared:

TABLE 5

| Example No. | 2-chloro-3-nitrobiphenyl Starting Material | Compound of Formula XVII |
|---|---|---|
| 27 | (2-chloro-3-nitrobiphenyl) | (2-(N—methylamino)-3-nitrobiphenyl) |
| 28 | (2-chloro-3-nitro-6-fluorobiphenyl) | (6-fluoro-2-(N—methylamino)-3-nitrobiphenyl) |
| 29 | (2,6-di-chloro-3 nitro-6-biphenyl) | (6-chloro-2-(N—methylamino)-3-nitrobiphenyl) |
| 30 | (6-fluoro-1-(4'-methoxyphenyl)-2-chloro-3-nitrobenzene) | (6-fluoro-1-(4'-methoxyphenyl)-2-(N—methylamino)-3-nitrobenzene) |

EXAMPLES 31–34

Using the method described in Scheme III, step 2, and starting with the indicated intermediate, the following compounds of Formula XVIII may be prepared (Table 6):

TABLE 6

| Example No. | Compound of Formula XVII | Compound of Formula XVIII |
|---|---|---|
| 31 | Example 27 | (3-amino-2-(N—methylamino)biphenyl) |
| 32 | Example 28 | (3-amino-6-fluoro-2-(N—methylamino)biphenyl) |

TABLE 6-continued

| Example No. | Compound of Formula XVII | Compound of Formula XVIII |
|---|---|---|
| 33 | Example 29 | (3-amino-6-chloro-2-(N—methyl-amino)biphenyl) |
| 34 | Example 30 | (3-amino-6-fluoro-1-(4'-methoxy-phenyl)-2-(N—methyl-amino)benzene) |

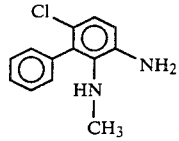

EXAMPLES 35–38

Using the method described in Scheme III, step 3, and starting with the indicated intermediate, the following compounds of Formula XIX may be prepared (Table 7):

TABLE 7

| Example No. | Compound of Formula XVIII | Compound of Formula XIX |
|---|---|---|
| 35 | Example 31 | (1,2-dihydro-1,3-dimethyl-2-keto-8-phenylquinoxaline) |
| 36 | Example 32 | (1,2-dihydro-1,3-dimethyl-7-fluoro-2-keto-8-phenylquinoxaline) |
| 37 | Example 33 | (7-chloro-1,2-dihydro-1,3-dimethyl-2-keto-8-phenylquinoxaline) |

TABLE 7-continued

| Example No. | Compound of Formula XVIII | Compound of Formula XIX |
|---|---|---|
| 38 | Example 34 | (1,2-dihydro-1,3-dimethyl-7-fluoro-2-keto-8-(4'-methoxyphenyl)quinoxaline) |

EXAMPLES 39–42

Using the method of Scheme III, step 4, and starting with the indicated intermediate, the following compounds of Formula XX may be prepared (Table 8):

TABLE 8

| Example No. | Compound of Formula XIX | Compound of Formula XX |
|---|---|---|
| 39 | Example 35 | (1,3-dimethyl-8-phenyl-1,2,3,4-tetrahydroquinoxaline) |
| 40 | Example 36 | (1,3-dimethyl-7-fluoro-8-phenyl-1,2,3,4-tetrahydroquinoxaline) |
| 41 | Example 37 | (7-chloro-1,3-dimethyl-8-phenyl-1,2,3,4-tetrahydroquinoxaline) |
| 42 | Example 38 | (1,3-dimethyl-7-fluoro-8-(4'-methoxyphenyl) 1,2,3,4-tetrahydroquinoxaline) |

EXAMPLES 43-46

Using the method of Scheme III, step 5, and starting with the indicated intermediate, the following compounds of Formula XXI may be prepared (Table 9):

TABLE 9

| Example No. | Compound of Formula XX | Compound of Formula XXI |
|---|---|---|
| 43 | Example 39 | 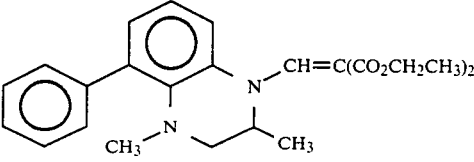<br>(ethyl-[4-(1,3-dimethyl-8-phenyl-1,2,3,4-tetrahydroquinoxalinyl)]methylenemalonate) |
| 44 | Example 40 | 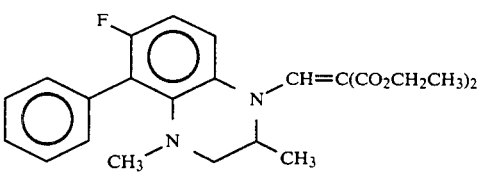<br>(ethyl[4-(1,3-dimethyl-7-fluoro-8-phenyl-1,2,3,4-tetrahydroquinoxalinyl)]methylenemalonate) |
| 45 | Example 41 | 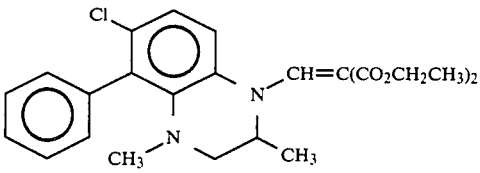<br>(ethyl[4-(7-chloro-1,3-dimethyl-8-phenyl-1,2,3,4-tetrahydroquinoxalinyl)]methylenemalonate) |
| 46 | Example 42 | 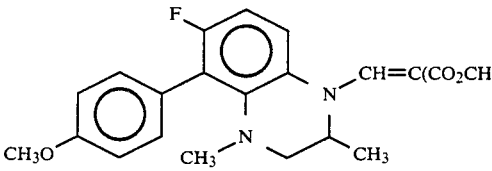<br>(ethyl[4-(1,3-dimethyl-7-fluoro-8-(4'-methoxyphenyl)-1,2,3,4-tetrahydroquinoxalinyl)]methylenemalonate) |

EXAMPLES 47-50

Using the method of Scheme III, steps 6 and 7, and starting with the indicated intermediate, the following compounds of Formula XXII may be prepared (Table 10):

TABLE 10

| Example No. | Compound of Formula XXI | Compound of Formula XXII |
|---|---|---|
| 47 | Example 43 | 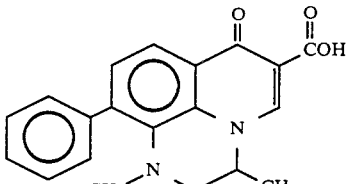<br>(2,3-dihydro-1,3-dimethyl-7-oxo-10-phenyl-1H,7H—pyrido[1,2,3-de]quinoxaline-6-carboxylic acid) |
| 48 | Example 44 | 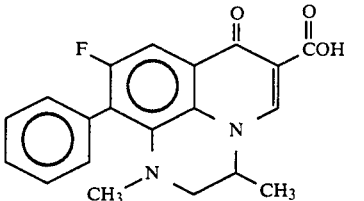<br>(2,3-dihydro-1,3-dimethyl-9-fluoro-7-oxo-10-phenyl-1H,7H—pyrido[1,2,3-de]quinoxaline-6-carboxylic acid) |
| 49 | Example 45 | 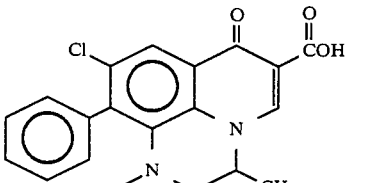 |

TABLE 10-continued

| Example No. | Compound of Formula XXI | Compound of Formula XXII |
|---|---|---|
| | | (9-chloro-2,3-dihydro-1,3-dimethyl-7-oxo-10-phenyl-1H,7H—pyrido[1,2,3-de]-quinoxaline-6-carboxylic acid) |
| 50 | Example 46 | 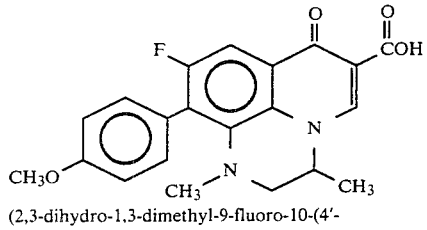 (2,3-dihydro-1,3-dimethyl-9-fluoro-10-(4'-methoxyphenyl)-7-oxo-1H,7H—pyrido[1,2,3-de]quinoxaline-6-carboxylic acid) |

EXAMPLES 50-53

Using the method described in Scheme IV, step 1, and starting with the indicated 2-methyl-4-oxo-4,5,6,7-tetrahydroindoles of Formula XXIV and the indicated phenyl Grignard reagents, the following compounds of Formula XXV may be prepared (Table 11):

TABLE 11

| Example No. | Compound of Formula XXIV | Grignard Reagent | Compound of Formula XXV |
|---|---|---|---|
| 50 | | | (4-hydroxy-2-methyl-4-phenyl-4,5,6,7-tetrahydroindole) |
| 51 | | | (4-hydroxy-4-(4'-methoxyphenyl)-2-methyl-4,5,6,7-tetrahydroindole) |
| 52 | | | (2,6-dimethyl-4-hydroxy-4-phenyl-4,5,6,7-tetrahydroindole) |
| 53 | | | (4-(4'-fluorophenyl)-4-hydroxy-2-methyl-4,5,6,7-tetrahydroindole) |

EXAMPLES 54–57

Using the method described in Scheme IV, step 2, and starting with the indicated intermediates of Formula XXV, the following compounds of Formula XXVI may be prepared (Table 12):

TABLE 12

| Example No. | Compound of Formula XXV | Compound of Formula XXVI |
|---|---|---|
| 54 | Example 50 | (2-methyl-4-phenylindole) |
| 55 | Example 51 | (4-(4'-methoxyphenyl)-2-methylindole) |
| 56 | Example 52 | (2,6-dimethyl-4-phenylindole) |
| 57 | Example 53 | (4-(4'-fluorophenyl)-2-methylindole) |

EXAMPLES 58–61

Using the method described in Scheme IV, step 3, and starting with the indicated intermediates of Formula XXVI, the following compounds of Formula XXVII may be prepared (Table 13):

TABLE 13

| Example No. | Compound of Formula XXVI | Compound of Formula XXVII |
|---|---|---|
| 58 | Example 54 | (2,3-dihydro-2-methyl-4-phenylindole) |
| 59 | Example 55 | (2,3-dihydro-4-(4'-methoxyphenyl)-2-methylindole) |
| 60 | Example 56 | (2,3-dihydro-2,6-dimethyl-4-phenylindole) |
| 61 | Example 57 | (2,3-dihydro-4-(4'-fluorophenyl)-2-methylindole) |

EXAMPLES 62–65

Using the method described in Scheme IV, step 4, and starting with the indicated intermediates of Formula XXVII, the following compounds of Formula XXVIII may be prepared (Table 14):

TABLE 14

| Example No. | Compound of Formula XXVII | Compound of Formula XXVIII wherein R₃ is Et |
|---|---|---|
| 62 | Example 58 | (ethyl[2,3-dihydro-2-methyl-4-phenylindolyl]methylenemalonate) |
| 63 | Example 59 | (ethyl[2,3-dihydro-4-(4'-methoxyphenyl)-2-methylindolyl]methylenemalonate) |
| 64 | Example 60 | (ethyl(2,3-dihydro-2,6-dimethyl-4-phenylindolyl)methylenemalonate) |
| 65 | Example 61 | (ethyl[2,3-dihydro-4-(4'-fluorophenyl)-2-methylindolyl]methylenemalonate) |

EXAMPLES 66–69

Using the method described in Scheme IV, steps 5 and 6, and starting with the indicated intermediates of Formula XXVIII, the following compounds of Formula XXX may be prepared (Table 15):

TABLE 15

| Example No. | Compound of Formula XXVIII wherein R₃ is Et | Compound of Formula XXX |
|---|---|---|
| 66 | Example 62 | (1,2-dihydro-2-methyl-6-oxo-9-phenyl-6H—pyrrolo[3,2,1-ij]quinoline-5-carboxylic acid) |
| 67 | Example 63 | (1,2-dihydro-9-(4'-methoxyphenyl)-2-methyl-6-oxo-6H—pyrrolo[3,2,1-ij]-quinoline-5-carboxylic acid) |

| Example No. | Compound of Formula XXVIII wherein $R_3$ is Et | Compound of Formula XXX |
|---|---|---|
| 68 | Example 64 | 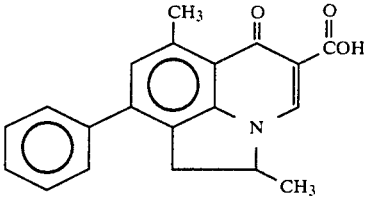<br>(1,2-dihydro-2,7-dimethyl-6-oxo-9-phenyl-6H—pyrrolo[3,2,1-ij]-quinoline-5-carboxylic acid) |
| 69 | Example 65 | 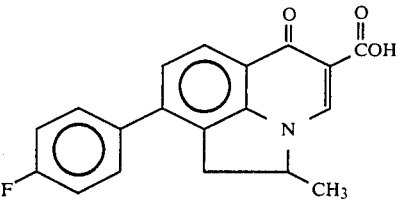<br>(1,2-dihydro-9-(4'-fluorophenyl)-2-methyl-6-oxo-6H—pyrrolo[3,2,1-ij]-quinoline-5-carboxylic acid) |

What is claimed is:

1. A compound of the formula

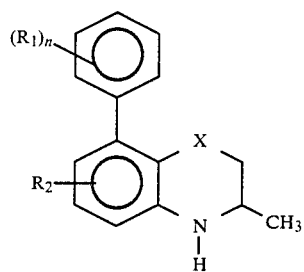

wherein X is selected from the group consisting of —O—, —CH$_2$— and

$R_1$ is selected from the group consisting of hydrogen, nitro, amino, lower alkyl, lower alkanamido, lower N,N-dialkylamino, formamido, hydroxy, lower alkoxy, halogen, lower haloalkanamido, and pyrryl; n is 1 or 2; and $R_2$ is selected from the group consisting of hydrogen, methyl, fluoro, chloro and nitro.

2. A compound of the formula

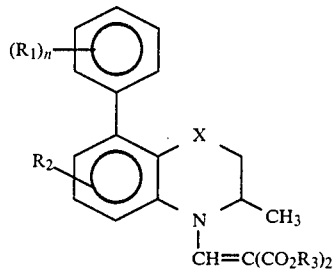

wherein X is selected from the group consisting of —O—, —CH$_2$— and

$R_1$ is selected from the group consisting of hydrogen, nitro, amino, lower alkyl, lower alkanamido, lower N,N-dialkylamino, formamido, hydroxy, lower alkoxy, halogen, lower haloalkanamido, and pyrryl; n is 1 or 2; $R_2$ is selected from the group consisting of hydrogen, methyl, fluoro, chloro and nitro; and $R_3$ is lower alkyl.

* * * * *